(12) United States Patent
Pond, Jr. et al.

(10) Patent No.: US 7,927,360 B2
(45) Date of Patent: Apr. 19, 2011

(54) SPINAL ANCHOR ASSEMBLIES HAVING EXTENDED RECEIVERS

(75) Inventors: John D. Pond, Jr., Germantown, TN (US); Anthony J. Melkent, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 619 days.

(21) Appl. No.: 11/341,274

(22) Filed: Jan. 26, 2006

(65) Prior Publication Data
US 2007/0191840 A1 Aug. 16, 2007

(51) Int. Cl.
*A61B 17/70* (2006.01)
(52) U.S. Cl. ....... 606/265; 606/86 A; 606/267; 606/269; 606/270; 606/319
(58) Field of Classification Search .......... 606/264–278, 606/300, 301, 305, 306, 319, 86 A
See application file for complete search history.

(56) References Cited

U.S. PATENT DOCUMENTS

| | | | |
|---|---|---|---|
| 4,448,191 A | 5/1984 | Rodnyansky | |
| 5,020,519 A | 6/1991 | Hayes | |
| 5,242,443 A | 9/1993 | Kambin | |
| 5,720,751 A | 2/1998 | Jackson | |
| 5,910,141 A | 6/1999 | Morrison et al. | |
| 6,183,472 B1 | 2/2001 | Lutz | |
| 6,226,548 B1 | 5/2001 | Foley et al. | |
| 6,235,028 B1 | 5/2001 | Brumfield et al. | |
| 6,485,491 B1 | 11/2002 | Farris et al. | |
| 6,530,929 B1 | 3/2003 | Justis et al. | |
| 6,648,888 B1 | 11/2003 | Schluzas | |
| 6,660,006 B2 | 12/2003 | Markworth et al. | |
| 6,740,086 B2* | 5/2004 | Richelsoph | 606/60 |
| 6,740,089 B2 | 5/2004 | Haider | |
| 6,821,277 B2 | 11/2004 | Teitelbaum et al. | |
| 7,160,300 B2* | 1/2007 | Jackson | 606/273 |
| 7,179,261 B2* | 2/2007 | Sicvol et al. | 606/86 A |
| 7,250,052 B2* | 7/2007 | Landry et al. | 606/86 A |
| 2002/0161368 A1 | 10/2002 | Foley et al. | |
| 2003/0130659 A1 | 7/2003 | Haider | |
| 2003/0199873 A1* | 10/2003 | Richelsoph | 606/61 |
| 2003/0199884 A1 | 10/2003 | Davison et al. | |
| 2003/0225408 A1 | 12/2003 | Nichols et al. | |
| 2004/0039384 A1 | 2/2004 | Boehm, Jr. et al. | |
| 2004/0049191 A1 | 3/2004 | Markworth et al. | |
| 2004/0138662 A1 | 7/2004 | Landry et al. | |
| 2004/0143265 A1 | 7/2004 | Landry et al. | |
| 2004/0162560 A1* | 8/2004 | Raynor et al. | 606/73 |
| 2004/0172022 A1 | 9/2004 | Landry et al. | |
| 2004/0215190 A1 | 10/2004 | Nguyen et al. | |

(Continued)

FOREIGN PATENT DOCUMENTS

DE 20 2005 007 495 U1 8/2005

*Primary Examiner* — Eduardo C Robert
*Assistant Examiner* — Ellen C Hammond

(57) ABSTRACT

There are provided systems and methods for positioning a connecting member adjacent the spinal column that include one or more anchor assemblies having an anchor engageable to bony structure and an extended receiver having a guide portion and an implantation portion. A connecting member is movable along the guide portion from a location outside the patient to the implantation portion in the patient, where the connecting member is secured to the anchor assembly with an engaging member. The guide portion is formed as a single unit with but separable from the implantation portion to provide a modified low-profile anchor assembly after implantation of the connecting member.

15 Claims, 12 Drawing Sheets

U.S. PATENT DOCUMENTS

| | | |
|---|---|---|
| 2004/0267275 A1 | 12/2004 | Cournoyer et al. |
| 2005/0010219 A1 | 1/2005 | Dalton |
| 2005/0010221 A1 | 1/2005 | Dalton |
| 2005/0033299 A1 | 2/2005 | Shluzas |
| 2005/0080418 A1 | 4/2005 | Simonson et al. |
| 2005/0085813 A1 | 4/2005 | Spitler et al. |
| 2005/0131408 A1* | 6/2005 | Sicvol et al. .................. 606/61 |
| 2005/0131421 A1 | 6/2005 | Anderson et al. |
| 2005/0131422 A1 | 6/2005 | Anderson et al. |
| 2005/0137594 A1* | 6/2005 | Doubler et al. ................ 606/61 |
| 2005/0154389 A1 | 7/2005 | Sclover et al. |
| 2005/0171540 A1 | 8/2005 | Lim et al. |
| 2005/0182407 A1 | 8/2005 | Dalton |
| 2005/0182410 A1* | 8/2005 | Jackson ......................... 606/73 |
| 2005/0192570 A1 | 9/2005 | Jackson |
| 2005/0192579 A1 | 9/2005 | Jackson |
| 2005/0192589 A1 | 9/2005 | Raymond et al. |
| 2005/0273101 A1* | 12/2005 | Schumacher .................. 606/61 |
| 2006/0025771 A1* | 2/2006 | Jackson ......................... 606/61 |
| 2006/0036252 A1 | 2/2006 | Baynham et al. |
| 2006/0058794 A1* | 3/2006 | Jackson ......................... 606/61 |
| 2006/0084980 A1* | 4/2006 | Melkent et al. ................ 606/61 |
| 2006/0293664 A1* | 12/2006 | Schumacher .................. 606/61 |
| 2008/0015584 A1* | 1/2008 | Richelsoph .................... 606/61 |
| 2008/0082103 A1* | 4/2008 | Hutton et al. .................. 606/73 |
| 2008/0119849 A1* | 5/2008 | Beardsley et al. ............. 606/61 |
| 2008/0119850 A1* | 5/2008 | Sicvol et al. ................... 606/61 |
| 2008/0300638 A1* | 12/2008 | Beardsley et al. ............ 606/306 |

* cited by examiner

US 7,927,360 B2

SPINAL ANCHOR ASSEMBLIES HAVING EXTENDED RECEIVERS

BACKGROUND

Orthopedic devices such as spinal rods, plates, tethers, staples and other devices can be secured along the spinal column between one or more vertebral levels to stabilize the one or more vertebral levels. While surgical procedures along the spinal column for placement of such devices are becoming less invasive, the decrease in space available in the approach to the surgical site and at the surgical site for handling and manipulating of the devices increases the difficulty in maneuvering, maintaining and finally positioning of the devices during the procedure. Furthermore, the small and intricate parts commonly associated with such orthopedic devices can increase the difficulty of the installation procedure. Accordingly, systems and devices which facilitate placement of orthopedic devices along the spinal column are desirable.

SUMMARY

There are provided systems and methods for positioning a connecting member adjacent the spinal column that include at least two anchor assemblies having an anchor engageable to bony structure and an extended receiver having a guide portion and an implantation portion. A connecting member is movable along the guide portion from a location outside the patient to the implantation portion in the patient, where the connecting member is secured to the anchor assembly with an engaging member. The guide portion is formed as a single unit with but separable from the implantation portion to provide a modified low-profile anchor assembly after implantation of the connecting member.

These and other aspects will be apparent from the following description of the illustrated embodiments.

DESCRIPTION OF THE ILLUSTRATED EMBODIMENTS

Figure 1:
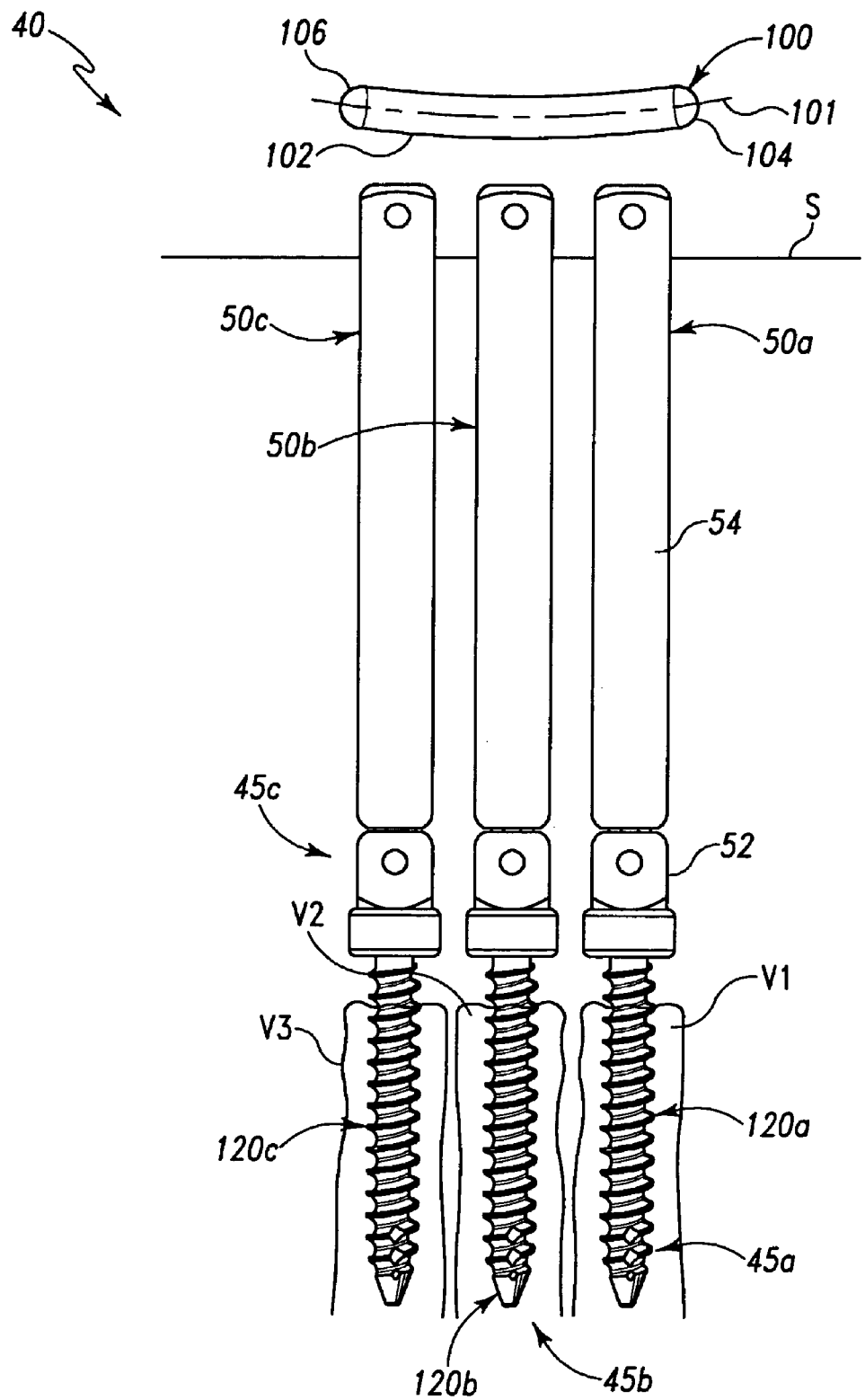
FIG. 1 is an elevation view a system for positioning a connecting member along the spinal column in a minimally invasive procedure.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices and described methods, and any such further applications of the principles of the invention as illustrated herein are contemplated as would normally occur to one skilled in the art to which the invention relates.

Referring to FIG. 1 there is shown a system 40 for positioning a connecting member 100 adjacent the spinal column in a minimally invasive surgical procedure. Although system 40 is particularly suited for minimally invasive surgical procedures, it is not restricted to such. Furthermore, although its use and application is described with regard to spinal surgery, applications in surgeries other than spinal surgery are also contemplated. In one form, system 40 provides at least a pair of anchors assemblies 45 including extended receivers 50 mounted to anchors 120 engaged to the spinal column. The extended receivers 50 extend proximally from the anchors 120, and guide the placement of a connecting member 100 from a position remote from the spinal column to a position adjacent the spinal column. The extended receivers 50 are configured so that when the connecting member 100 is adjacent the spinal column, connecting member 100 extends between the at least a pair of anchors 120. The connecting member 100 can be secured to the anchor assemblies 45 and provide stabilization of the spinal column segment to which the anchors 120 are attached. The extended receivers 50 can be modified without invasively accessing the patient's body after positioning of connecting member 100 to provide the anchor assemblies with a configuration suitable for post-operative implantation.

In one embodiment, each of the at least a pair of extended receivers 50 includes a distal implantation portion 52 adjacent the respective anchor 120 for receiving the connecting member 100 in an implantation position to stabilize one or more vertebral levels. A proximal guide portion 54 extends from opposite sides of the implantation portion 52 for guiding the connecting member 100 from a location outside the patient to its implantation location in the implantation portion 52 adjacent the anchors 120. The guide portion 54 defines a channel therethrough that opens along opposite sides of the extended receiver 50, and extends from the proximal end of the extended receiver 50 to the implantation portion 52. In another embodiment, guide portion 54 is formed as a single unit with implantation portion 52 portion at a break-off segment therebetween. The break-off segment provides a separation location between the implantation portion 52 and the guide portion 54 so that when sufficient force is applied to guide portion 54 it can be removed to modify the extended receiver 50 to an implantation configuration. In another embodiment, the at least a pair of anchor assemblies 45 includes three anchor assemblies 45.

In one embodiment, the connecting member 100 is an elongated rod and the anchors 120 are bone screws. The bone screws can be a multi-axial type screw positioned in the implantation portion 52 of extended receiver 50 so that the receiver and bone screw are pivotal relative to one another. In another embodiment, the bone screws are non-pivotal or fixed relative to the receiver. Connecting member 100 can be received in, on, or about the implantation portion 52 of extended receiver 50 for engagement thereto. The connecting member 100 can be rigid, semi-rigid, flexible, elastic, non-compression load bearing, or of other suitable form for extending between and stabilizing adjacent portions of the spinal column when secured thereto.

In FIG. 1, system 40 includes a first anchor assembly 45a engaged to vertebra V1 and having a first extended receiver 50a, a second anchor assembly 45b engaged to vertebra V2 having a second extended receiver 50b, and a third anchor assembly 45c engaged to vertebra V3 and having a third extended receiver 50c. Extended receivers 50a, 50b, and 50c are engaged to respective ones of a first anchor 120a, a second anchor 120b and a third anchor 120c, which are engageable to respective ones of three adjacent vertebrae V1, V2, V3, shown diagrammatically in FIG. 1. It should be understood, however, that the system and techniques discussed herein may employ only two extended receivers and two anchors, or three or more extended receivers and anchors. Extended receivers 50a, 50b, 50c extend proximally from the respective anchors 120a, 120b, 120c through the tissue along the spinal column such that their proximal ends project from or are adjacent the skin level S of the patient for access by the surgeon. Extended receivers 50a, 50b, and 50c define a minimally invasive path for delivery of connecting member 100 through the skin and tissue of the patient to the anchors engaged to the vertebrae. The minimally invasive path reduces and/or minimizes the tissue retraction and dissection required to accommodate delivery of connecting member 100 to the implantation location along the spinal column where it provides the desired external stabilization of one or more vertebral levels.

Figure 2:
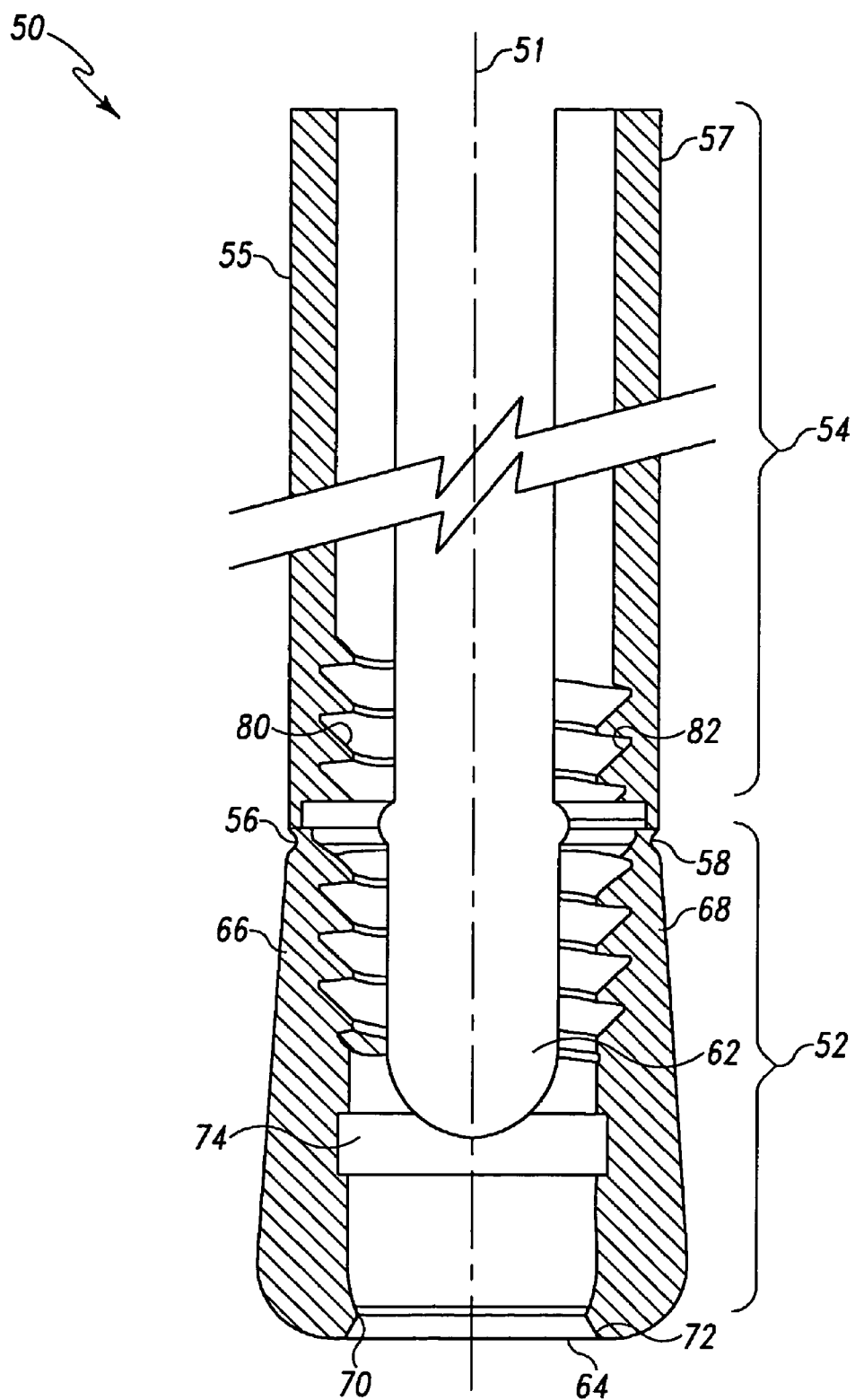
FIG. 2 is a sectional view of an extended receiver comprising a portion of the system of FIG. 1.

Referring now to FIG. 2, there is shown one embodiment of an extended receiver 50. Extended receiver 50 includes a lower or distal implantation portion 52 and an upper or proximal guide portion 54 extending along a central axis 51. Guide portion 54 includes a pair of arms 55, 57 formed as a single unit with but removable from implantation portion 52 at break-off regions 56, 58, respectively. Receiver 50 defines a general U-shape with a channel 62 extending therethrough transversely to central axis 51. A lower through-hole 64 extends along central axis 51 and opens at the bottom or distal end of implantation portion 52. In one embodiment, hole 64 is substantially perpendicular to channel 62.

Implantation portion 52 forms a saddle that houses anchor 120 and receives the connecting member 100 therethrough in an orthogonal or transverse orientation to central axis 51 and in an orientation generally parallel with the spinal column. Implantation portion 52 includes a pair of opposite side members 66, 68 sized and spaced to accommodate elongate member 100 therein. Arms 55, 57 form an extension of respective ones of the side members 66, 68, and are singularly formed therewith at the respective break-off region 56, 58. Arms 55, 57 include a length extending proximally from side members 66, 68 so that the proximal ends of arms 55, 57 are located outside the patient when anchor 120 is engaged to the spinal column. In one embodiment, this length is at least 30 millimeters. In another embodiment, the length of arms 55, 57 is at least 50 millimeters.

As further shown in FIG. 3, side members 66, 68 each include an internal thread profile 67, 69 that threadingly engages an engaging member 90 (as described below). Hole 64 is sized and shaped to receive and support anchor 120 therethrough. Near the bottom of implantation portion 52, hole 64 is narrowed by a wall portion 70. Below wall portion 70, hole 64 opens outwardly by virtue of a wall portion 72. Wall portion 72 allows anchor 120 to be positioned in any of an infinite number of angular positions relative to implantation portion 52 by reducing interference of the lower portion of implantation portion 52 with a shank portion 124 of anchor 120, while a head portion 122 of anchor 120 is supported on wall portion 70.

Other embodiments contemplate other engagement relationships between the anchor 120 and receiver 50. In one embodiment, anchor 120 is formed as a single unit with receiver 50 and extends along axis 51 in a uni-axial arrangement. In another embodiment, anchor 120 is captured in receiver 50 with a split-ring washer, collar, or other suitable retaining member. In still other embodiments, anchor 120 is pivotal in single plane, or in a predetermined number of planes, relative to receiver 50.

In the particular illustrated embodiment of implantation portion 52, implantation portion 52 includes an inner groove 74. As illustrated, groove 74 extends about side members 66, 68 and around hole 64. Groove 74 is configured to accommodate snap ring 76 in a compressed condition. Groove 74 can have a height that is, in one form, greater than a thickness of snap ring 76. Snap ring 76 can retain a crown 78 in implantation portion 52 about the proximal side of head 122 of anchor 120. Connecting member 100 is seated against crown 78 when secured in implantation portion 52 with engaging member 90. In one embodiment, seating of crown 78 locks anchor 120 in position relative to extended receiver 50. In such an embodiment, crown 78 and/or head 122 can include engagement structures that engage one another to provide the locked arrangement. In a further embodiment, at least some motion between the connecting member and anchor 120 is maintained by crown 78 when connecting member is secured in implantation portion 52. Still other embodiments contemplate that crown 78 can be omitted and that the connecting member 100 is seated directly against head 122 of anchor 120.

Figure 3:
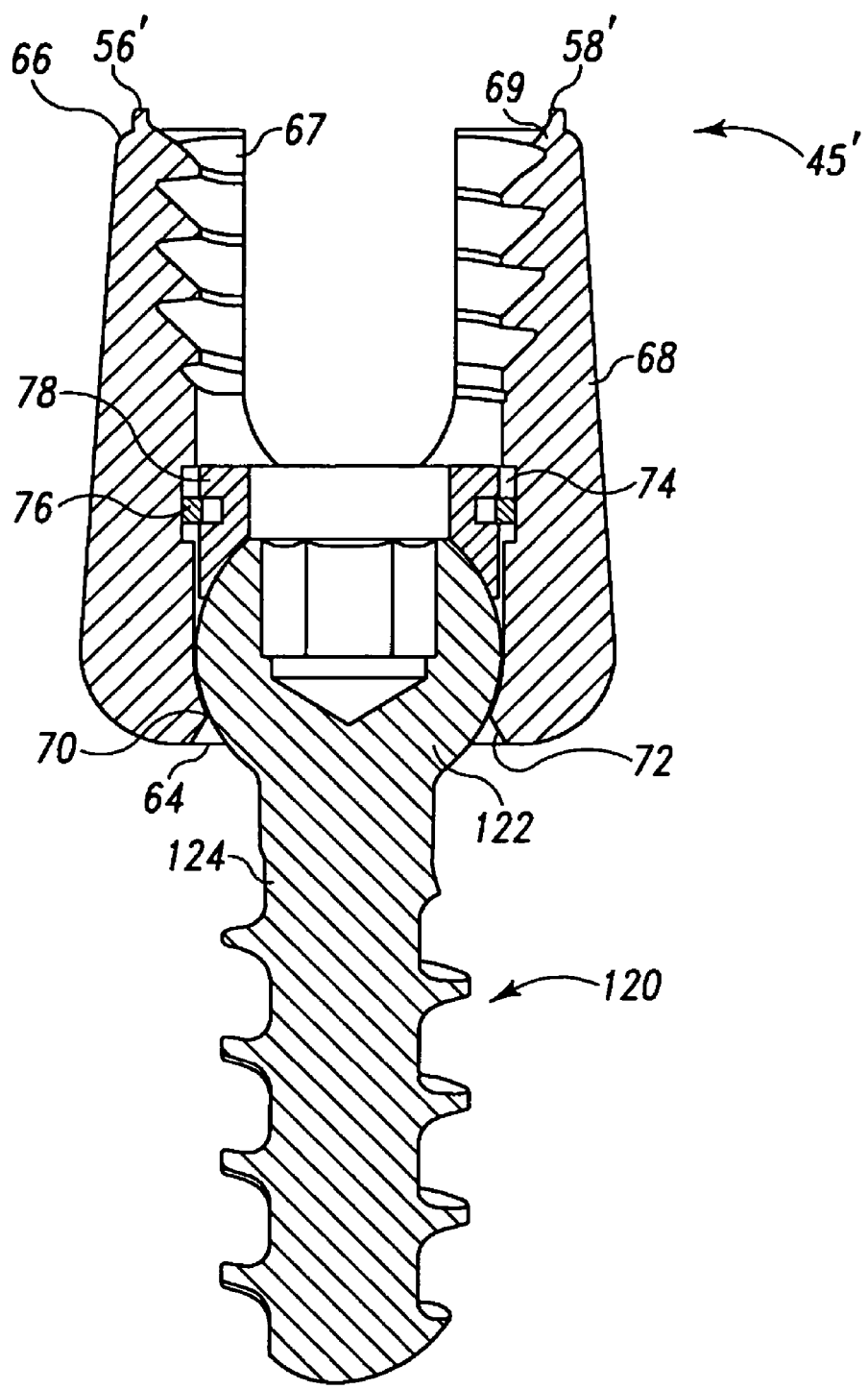
FIG. 3 is a sectional view of a modified extended receiver and anchor of an anchor assembly comprising a portion of the system of FIG. 1.

FIG. 3 further shows a modified anchor assembly 45' where arms 55, 57 have been severed at break-off regions 56, 58, forming modified break-off regions 56', 58'. Arms 55, 57 are removed after placement of connecting member 100 into implantation portion 52 and securement of engaging member 90 with internal threads 67, 69 of side members 66, 68. As shown in FIG. 2, arms 55, 57 can each include an internal thread profile 80, 82, respectively, that is threadingly engageable by engaging member 90 as it passes therethrough. The threaded engagement between arms 55, 57 and engaging member 90 provides a mechanical advantage in forcing connecting member 100 into implantation portion 52. When engaging member 90 is advanced distally into engagement with side members 66, 68, the connecting member 100 is firmly seated against crown 78, and engaging member 90 is secured to side members 66, 68

Figure 4:
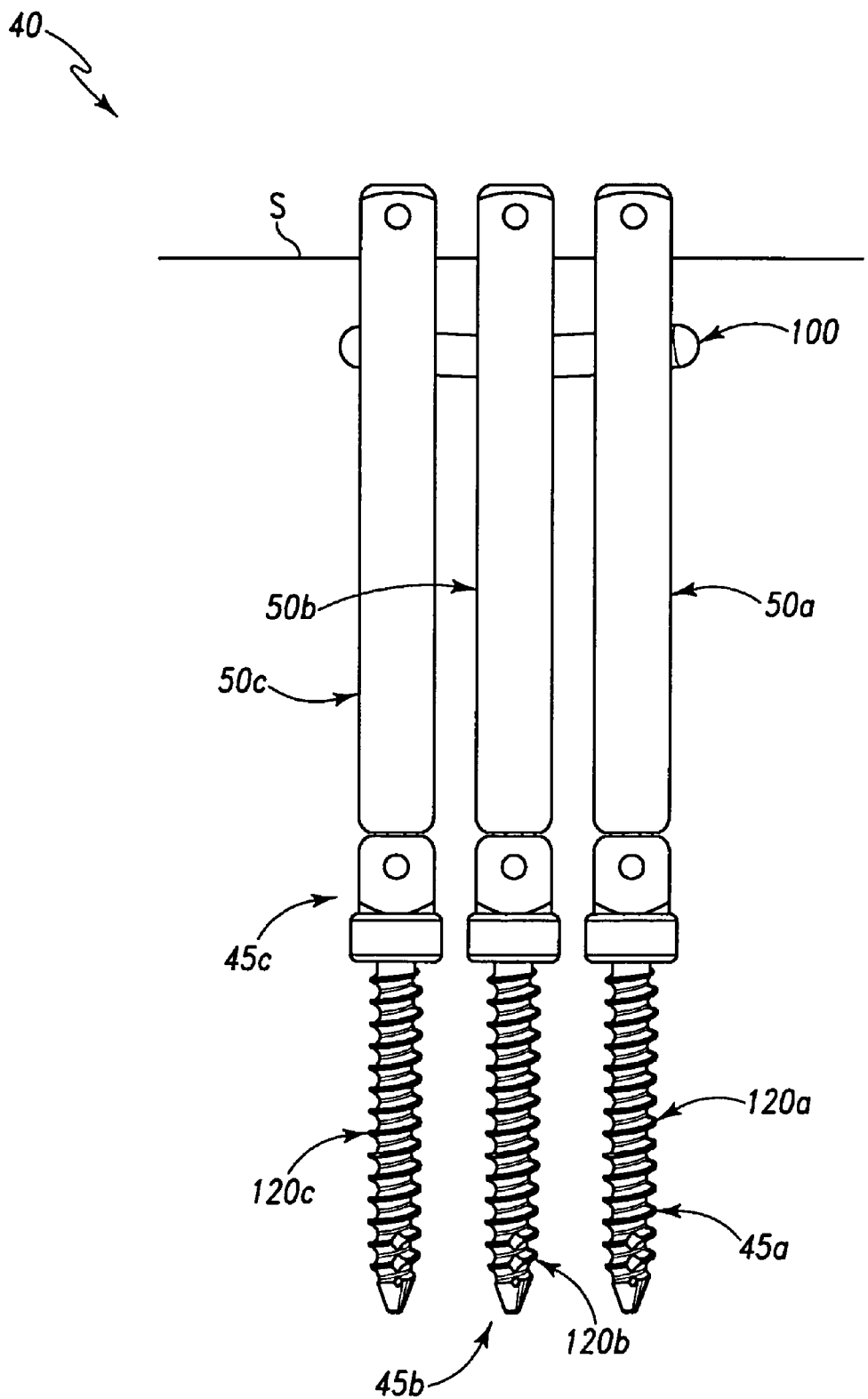
FIG. 4 is an elevation view of the system of FIG. 1 with a connecting member positioned in the extended receivers of the anchor assemblies.
Figure 5:
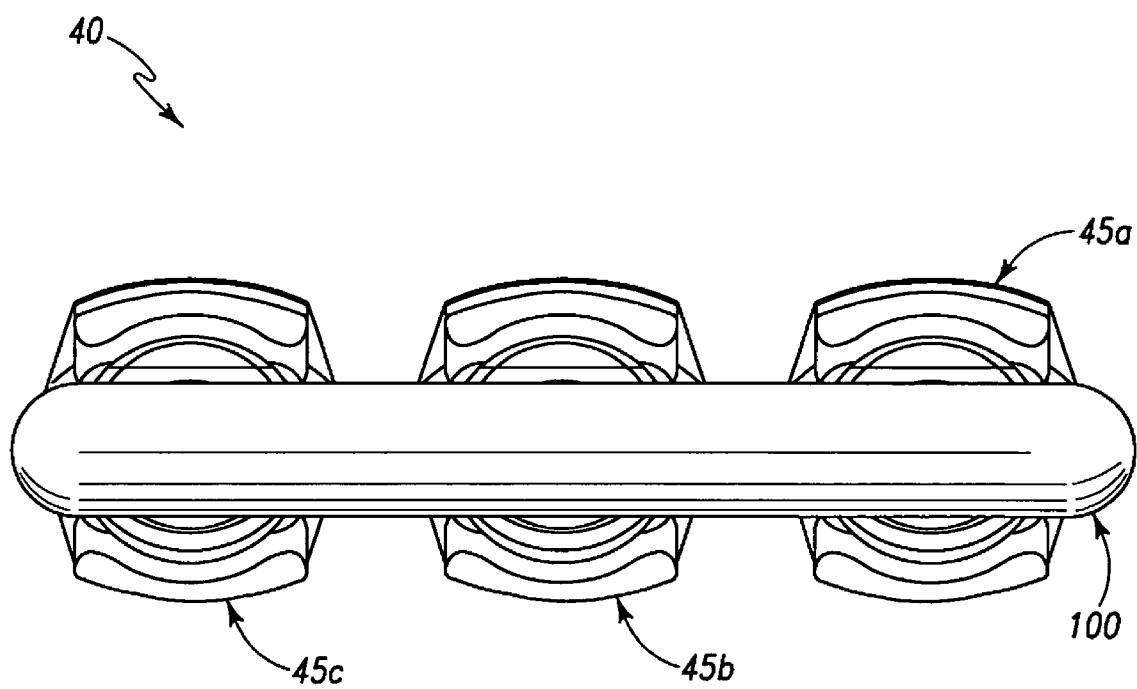
FIG. 5 is a plan view of the arrangement of FIG. 4.
Figure 6:
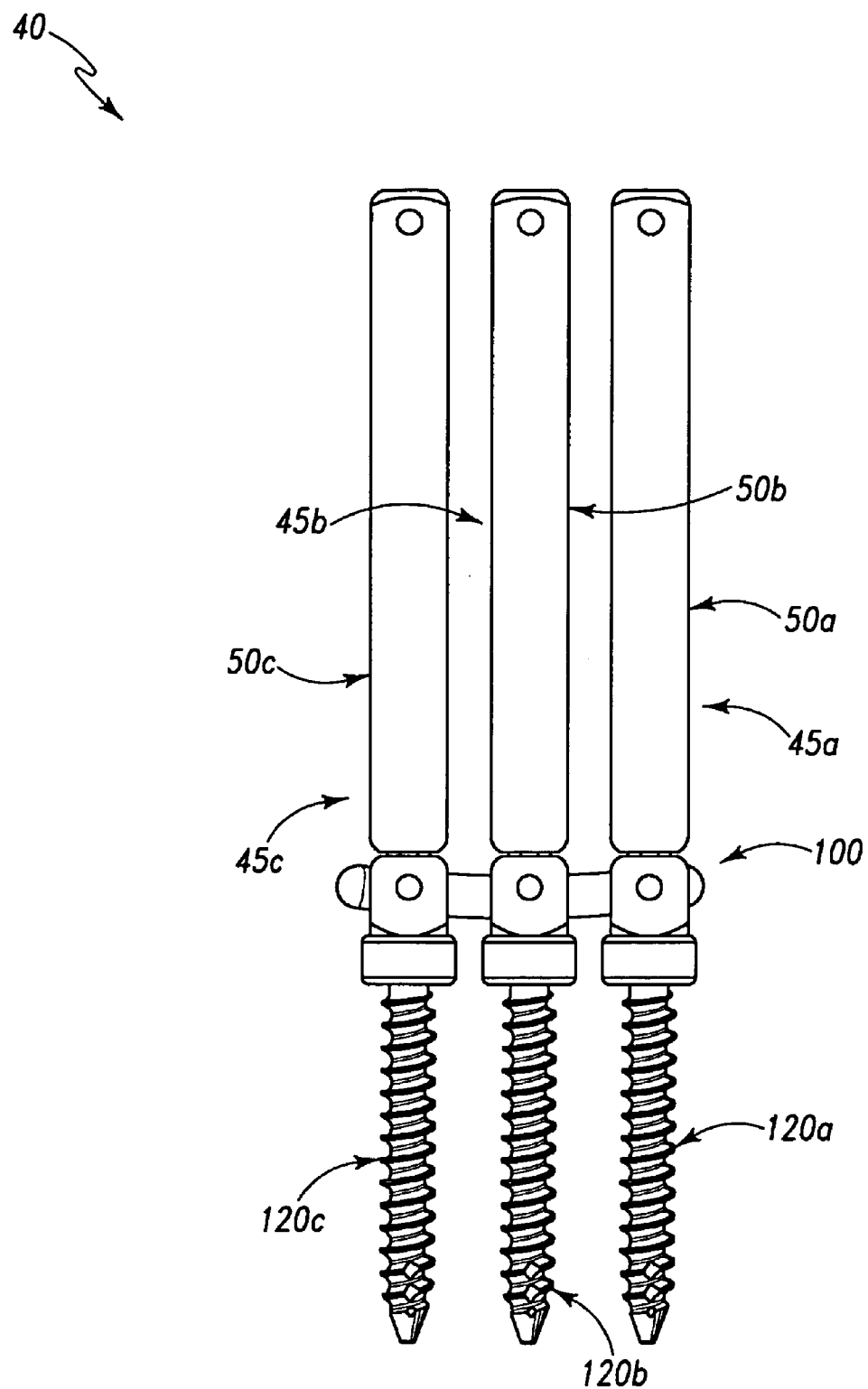
FIG. 6 is an elevation view of the system of FIG. 1 with a connecting member positioned in the implantation portions of the extended receivers of the anchor assemblies.

Referring now to FIGS. 4-12, various steps for implanting connecting member 100 and securing it along the spinal column in a minimally invasive surgical procedure employing system 40 will be discussed. In FIG. 4, connecting member 100 is positioned through the aligned channels 62 of extended receivers 50a, 50b, 50c. As shown in FIG. 5, connecting member 100 fits within and maintains the channels 62 in alignment when it is positioned therebetween. For extenders having multi-axial capabilities, one or more of the extenders 50*a*, 50*b*, 50*c* can be pivoted toward and/or away from the others as may be desired to facilitate placement of connecting member 100 therein. Connecting member 100 is moved below the skin level S and toward the spinal column until it is positioned in or adjacent implantation portions 52 of extended receivers 50, as shown in FIG. 6.

Figure 7:
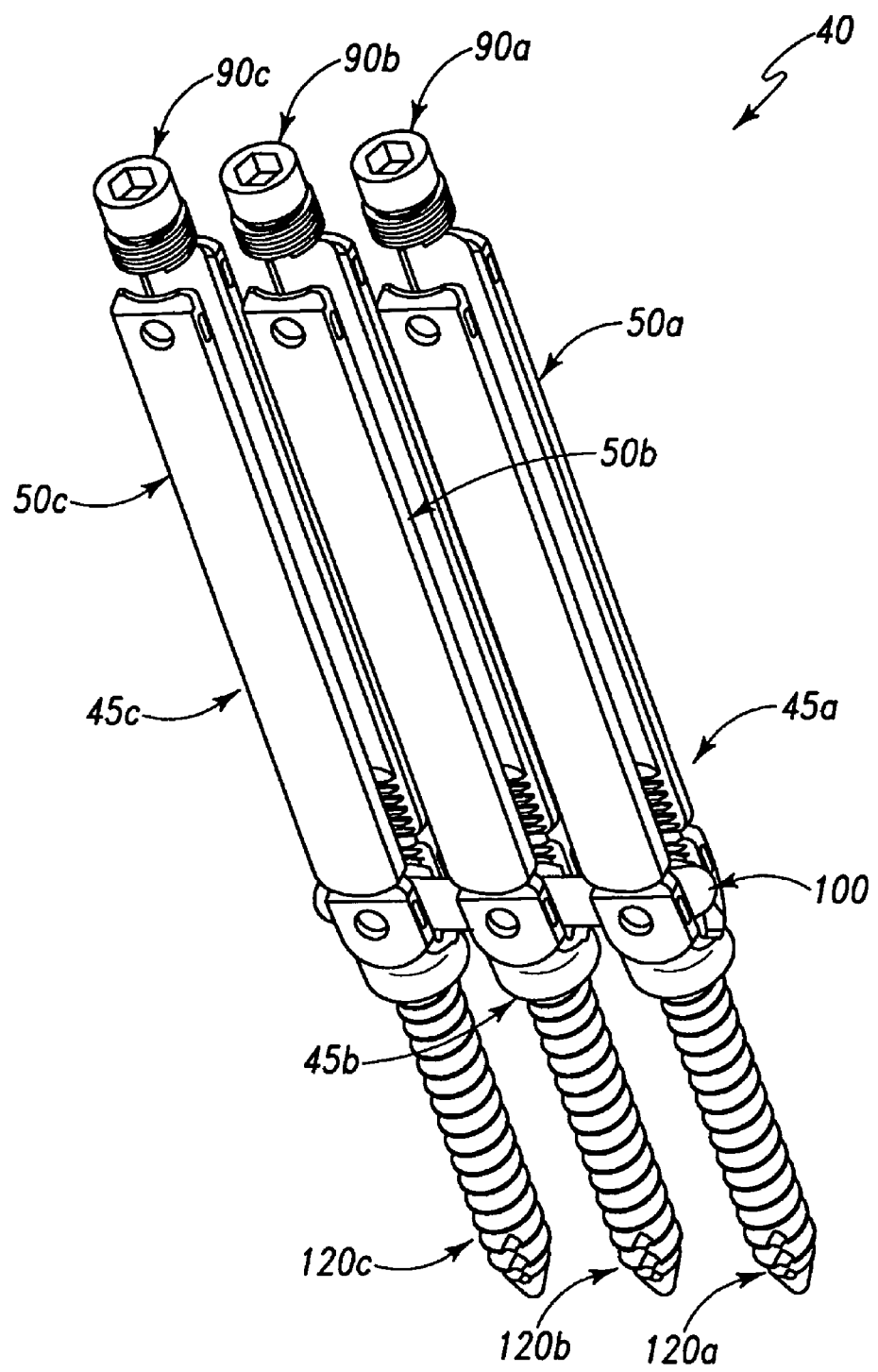
FIG. 7 is a perspective showing engaging members for positioning in the extended receivers to secure the connecting member in the implantation portions of the anchor assemblies.

In FIG. 7 engaging members 90*a*, 90*b*, 90*c* are provided for positioning through respective ones of the extended receivers 50*a*, 50*b*, 50*c*. Engaging members 90 can be in the form of a set screw having a distal externally threaded portion 92 and a proximal tool-engaging portion 94. Tool engaging portion 94 can be configured to break-off from distal portion 92 upon application of a sufficient force. Engaging members 90*a*, 90*b*, 90*c* can be secured to the respective implantation portions 52 of extended receivers 50 to secure connecting element 100 to the anchor assemblies 45.

Figure 8:
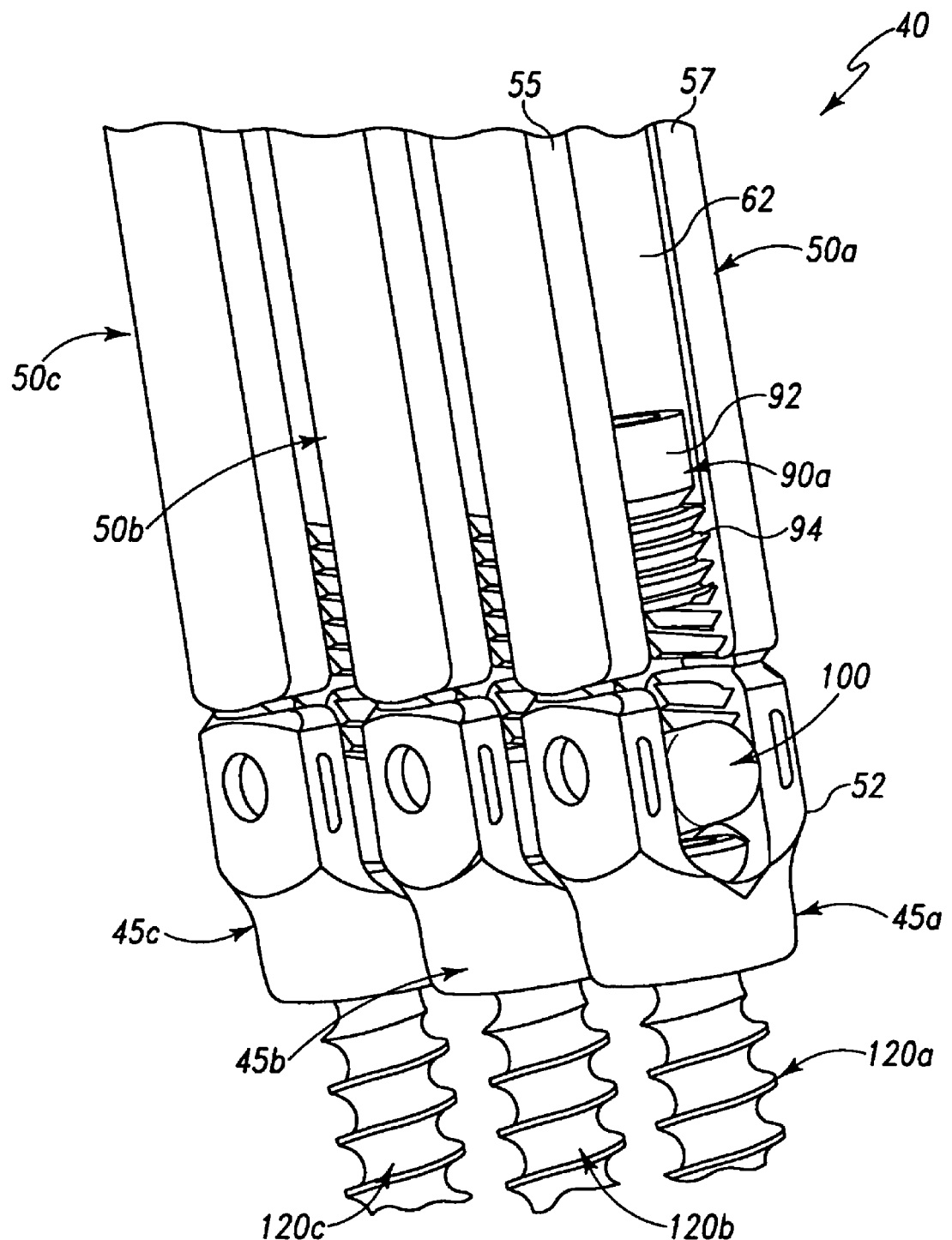
FIG. 8 is a perspective of a portion of the system showing one of the engaging members positioned in one of the extended receivers to secure the connecting member in the implantation portions of the anchor assemblies.
Figure 9:
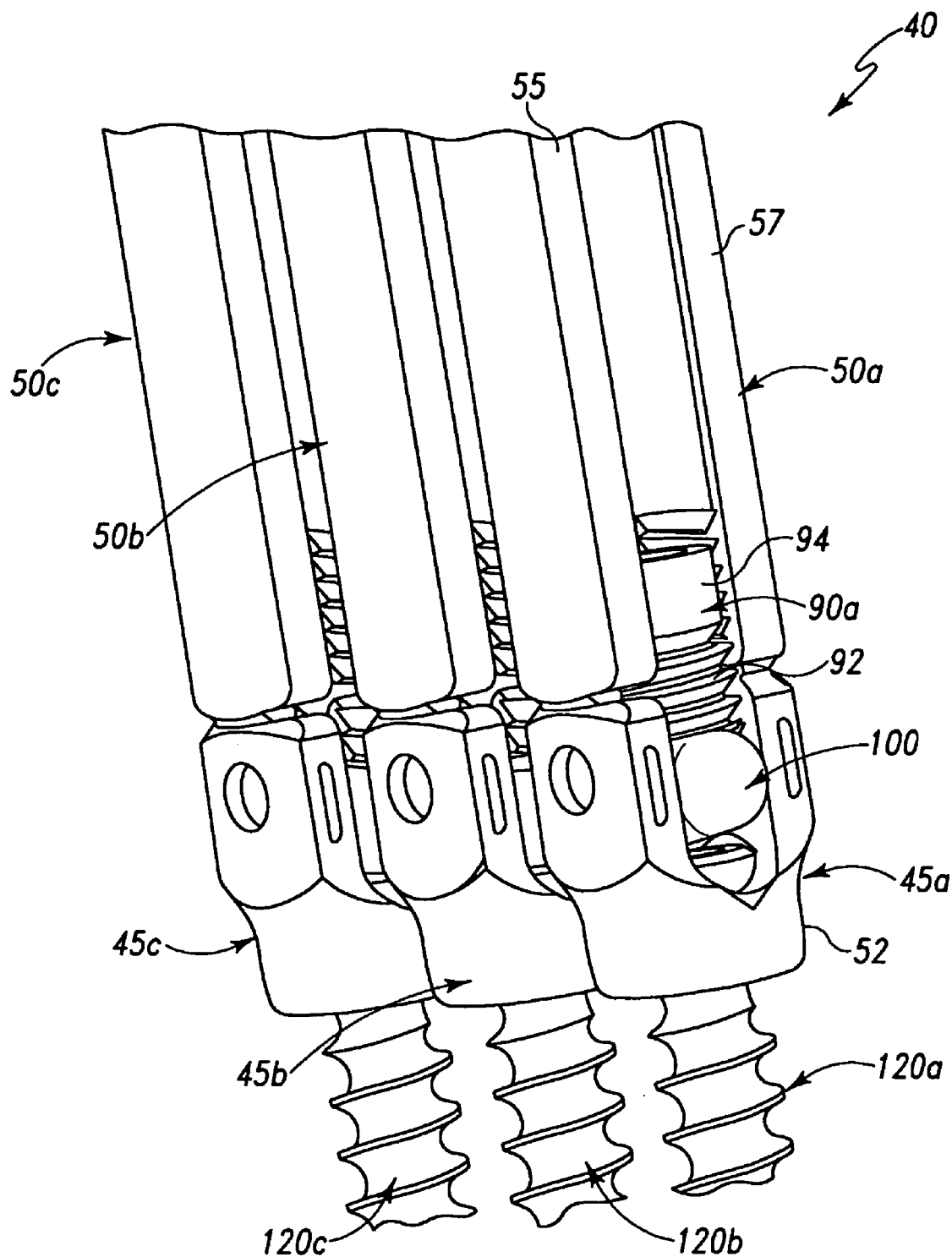
FIG. 9 is the view of FIG. 8 showing the engaging member engaged to the implantation portion of the extended receiver to secure the connecting member therein.

In FIG. 8, engaging member 90*a* is shown in threaded engagement with the internal threads along arms 55, 57 of guide portion 54 of extended receiver 50*a*. In instances wherein connecting member 100 is not full seated or positioned in implantation portion 52 of any one or more of the extended receivers, the respective engaging member 90 can act on the connecting member and reduce or force it into position into the implantation portion 52. The internal threads along arms 55, 57 provide a mechanical advantage in advancing the connecting member into the implanted position by bringing the vertebrae into alignment along connecting member 100. As shown in FIG. 9, engaging member 90*a* contacts connecting member 100 as engaging member 90 is threadingly advanced into engagement with the internal threads along side members 66, 68 of implantation portion 52.

Figure 10:
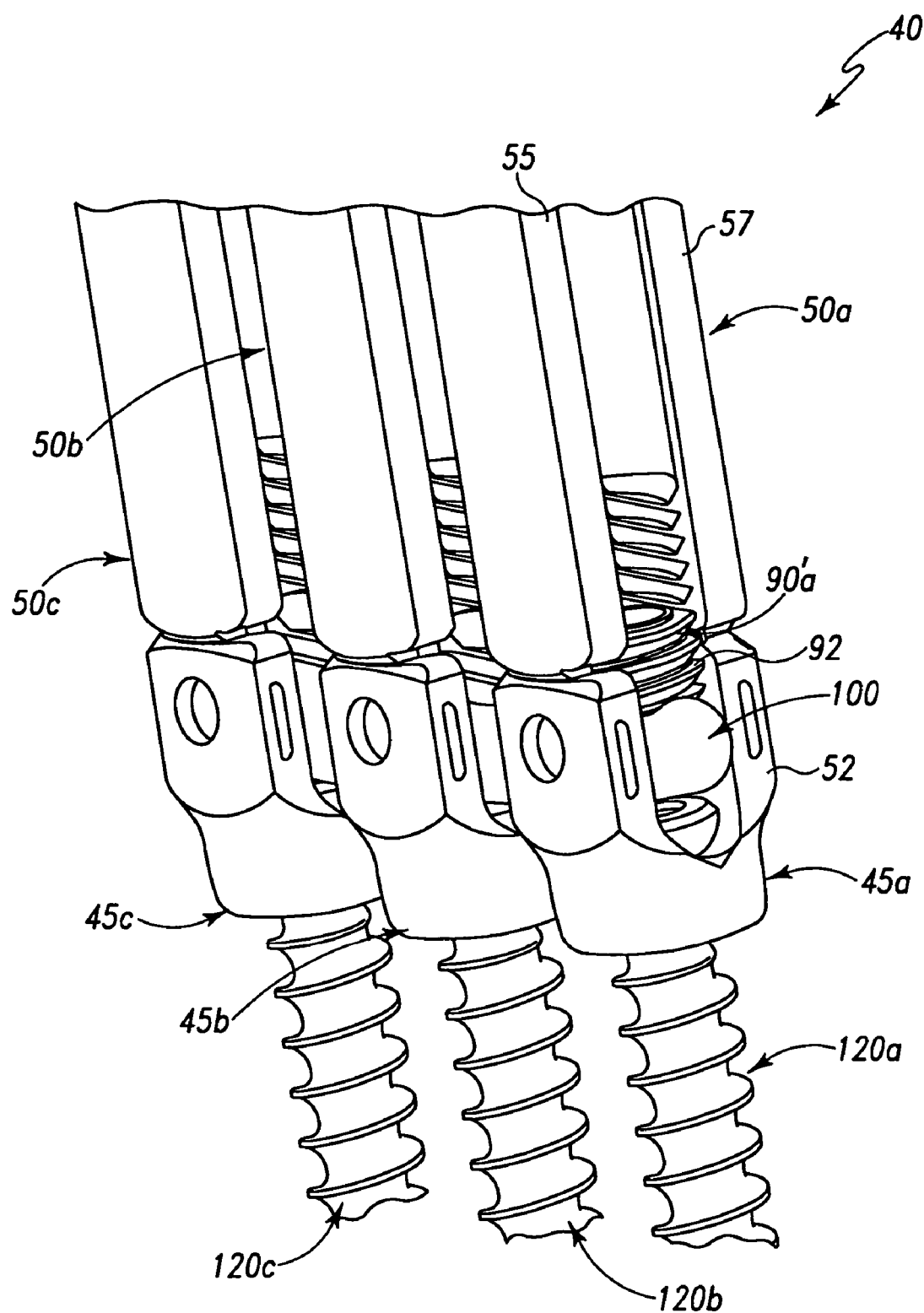
FIG. 10 is the view of FIG. 9 showing a proximal break-off portion of the engaging member removed upon application of sufficient force thereto.
Figure 11:
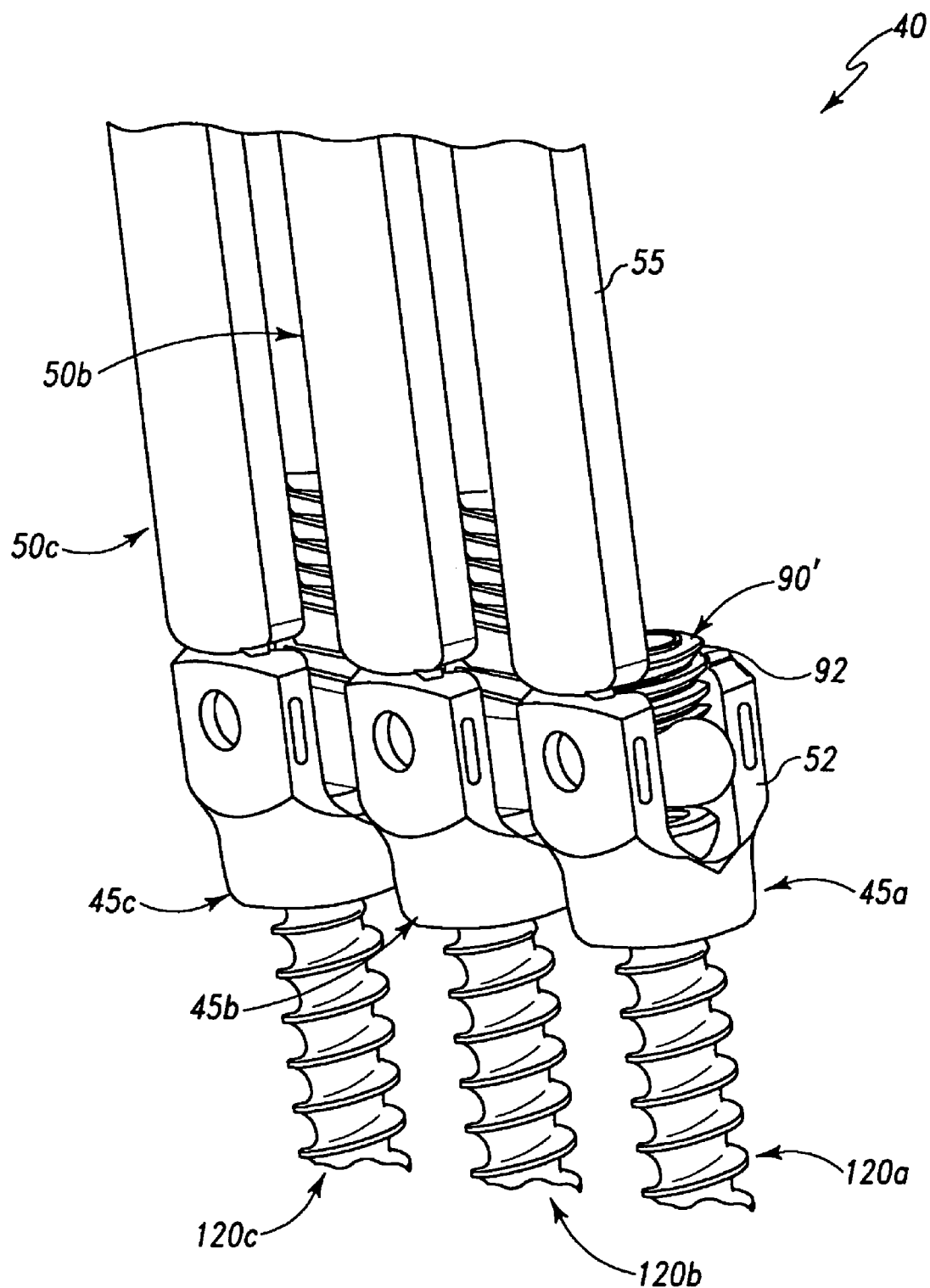
FIG. 11 is the view of FIG. 10 with one of the arms of the extended receiver separated from the implantation portion at a break-off region therebetween.
Figure 12:
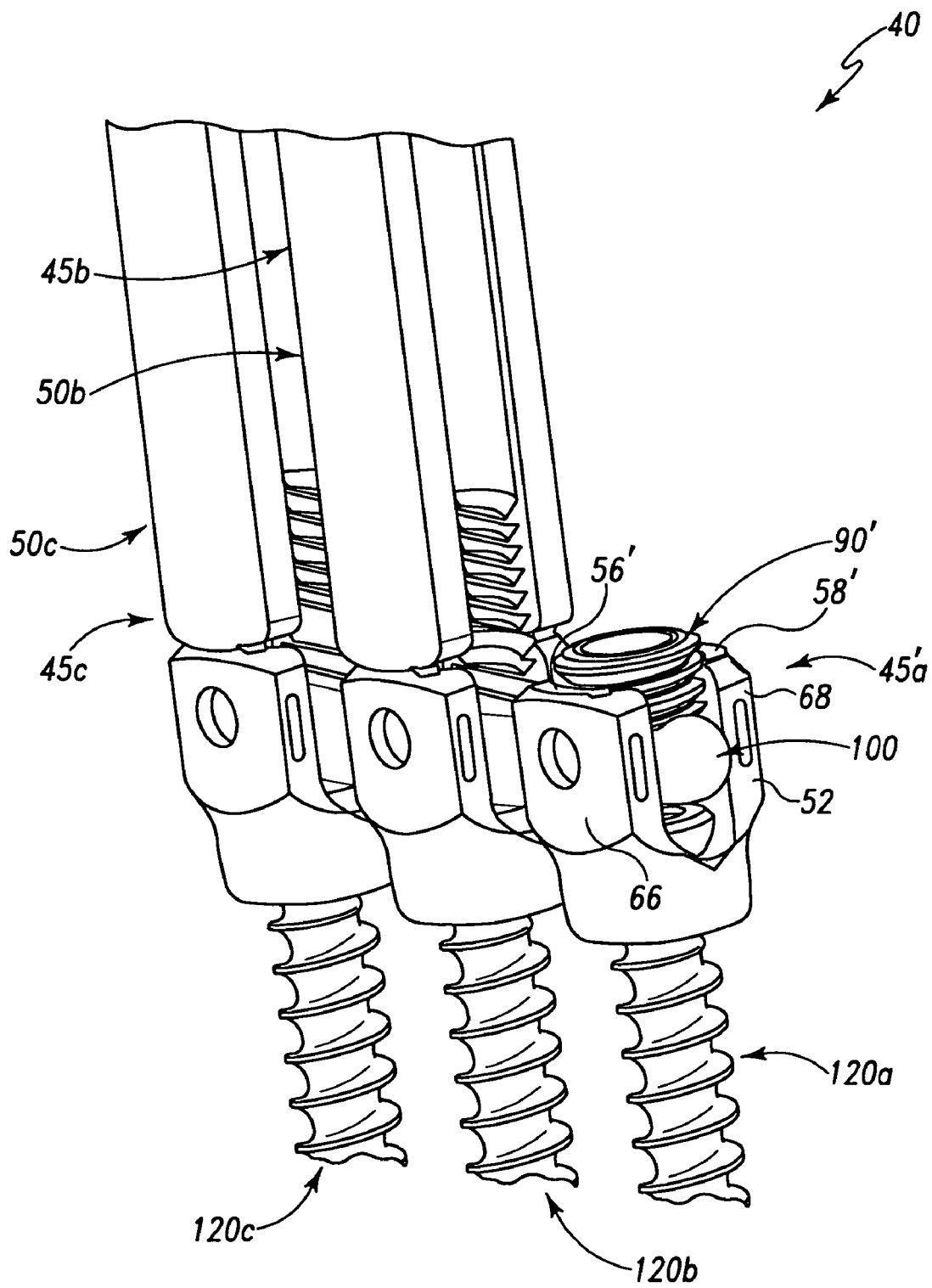
FIG. 12 is the view of FIG. 11 with the other arm of the extended receiver separated from the implantation portion at a second break-off region therebetween.

In FIG. 10 connecting element 100 is firmly seated in implantation portion 52 and sufficient torque applied to proximal portion 94 to sever it from distal portion 92, providing a modified engaging member 90*a*'. In this implanted position, engaging member 90*a*' can be recessed into implantation portion 52 so that it engages the threads along side members 66, 68. In FIG. 11, arm 57 has been separated from implantation portion 52 by applying sufficient torque, twisting, bending or shearing forces to the proximal end of arm 57 to sever it at break-off region 58 at side member 68. In FIG. 12, arm 55 has been separated from implantation portion 52 by applying sufficient removal force at the proximal end of arm 55 to sever it at break-off region 56 at side member 66. Arms 55, 57 include sufficient rigidity along their length to transmit the removal force applied to the proximal end to the respective break-off region without twisting, deforming or severing at a location proximal of the break-off region. This allows the minimally invasive access to be maintained without tissue retraction to access arms 55, 57 at locations within the patient to apply the removal force. Connecting member 100 is thus secured for post-operative implantation to a modified anchor assembly 45*a*' having a suitably low profile for post-operative implantation. The other anchors assemblies 45*b*, 45*c* can be similarly modified after securement of connecting member 100 therein to provide a low profile for system 40 extending from the spinal column.

Break-off regions 56, 58 provide an area of reduced wall thickness adjacent the distal end of the respective arm 55, 57 that extends between the arm 55, 57 and the respective side member 66, 68. Break-off regions 56, 58 can be located between the internal thread profiles defined by side members 66, 68 and the adjacent arms 55, 57. As shown in FIG. 2, break-off regions 56, 58 each include a groove in the inner side of the respective arm 55, 57 that extends outwardly from the major diameter of the internal thread and into the respective arm 55, 57 and the extension of the groove in the inner side of arms 55, 57 is greater than the major diameter of the internal thread of the respective arm 55, 57 and side member 66, 68. In the illustrated embodiment, the outer surface of each of the break-off regions 56, 58 forms a concave depression or recess that extends completely about arm 55, 57 and the respective adjacent side member 66, 68. Each of the arms 55, 57 is joined to the respective side member 66, 68 with a break-off region having a wall thickness that is reduced comparatively to an adjacent wall thickness of the respective arm and the respective side member. Other embodiments contemplate other techniques for reducing the wall thickness to provide a break-off region, such as by providing perforations or undercuts between the arms 55, 57 and the respective adjacent side member 66, 68. In any event, the break-off regions provide a separation location that is generally uniform and substantially free of sharp of jagged edges after separation of the respective arms 55, 57. Other embodiments contemplate a break-off region that is in a thread-free-zone.

It may also be desirable to provide a desired alignment between vertebrae by reducing the connecting member into the implantation portion of the extended receivers of the anchor assemblies. For example, the vertebrae may be misaligned as a result of spondylolisthesis, anatomical differences between the vertebrae, or some other condition. Also, there may be slight misalignments between the receiver members that make manually positioning the connecting member into each of the receiver members difficult. In such situations, the engaging members 90 can be employed to provide a mechanical advantage to seat the connecting member in the implantation portions as the engaging members are threadingly advanced along the arms 55, 57 and into the side members 66, 68.

System 40 may employ various instruments to facilitate selection of the connecting member, placement of the connecting member through the extenders and to the anchors, securement of the connecting member to the anchors, and manipulation of the vertebrae and/or anchors to a desired position or condition. For example, a driver can be provided that is positionable through any one of the extended receivers to engage the anchor to the vertebra. A driver for positioning the engaging member through the extended receiver and into engagement with the implantation portion can also be provided. A counter-torque device such as a wrench or handle arm, can be secured to any one of the extended receivers to hold the extended receiver in position relative to the anchor attached thereto as torque is applied to seat the engaging member into contact with the connecting member in the implantation portion of the extender receiver. Compressors and distractors can also be provided to facilitate application of a compressive or distraction force between anchors before final attachment of the connecting member to each anchor. Calipers can be provided to measure a distance between the outermost extended receivers for sizing of the length of the connecting member to be positioned between the anchors. A holding instrument can be provided that is adapted to grasp and hold the connecting member placed between the extenders, and can be employed to facilitate moving the connecting member distally along the extenders toward and into the anchors. A reduction instrument can be provided that is positionable along or about the extender receiver to provide a mechanical advantage for reduction of the connecting member into one or more of the implantation portions of the extended receivers.

Examples of suitable connecting members that extend between the anchors include rods, wires, tethers, strands, cables, bands, plates, and struts. The connecting member may include one component, or may include two or more components. One embodiment connecting member is shown in FIG. 1, and includes connecting member 100 having an elongated rod-shaped body 102. Body 102 extends along a longitudinal axis 101 between a first end 104 and an opposite second end 106. Body 102 is curved about a radius formed by longitudinal axis 101. Ends 104, 106 include generally the same size and shape, although such is not required. Other embodiments contemplate that body 102 is linear, a combination of linear and curved segments, a combination of linear segments angled relative to one another, or a combination of segments having differing curvatures. Body 102 has a uniform cross-section along its length, which can be circular as shown. However, non-uniform cross-sections are also contemplated. In one embodiment, connecting member is an elongated rod made from a metal alloy such as titanium. Other materials are also contemplated, including resorbable materials, non-resorbable material, polymers, elastomers, ceramics, other metals and metal alloys, shape memory materials, bone and bone substitute material, composites, and combinations of materials.

Each of the anchor assemblies can be attached to the respective vertebra using any one of a number of techniques. By way of example and not limitation, one embodiment of a procedure contemplates an incision over the target location of the spinal column, and that the skin and tissue are sequentially dilated to provide a minimally invasive pathway for anchor assembly insertion and engagement to each vertebra.

In another example procedure, a cannulated outer needle with an inner stylet can first be inserted to the targeted regions of the vertebrae, such as the pedicle in a posterior procedure, and aligned to provide the desired trajectory into the pedicle. Alignment can be monitored and checked with any viewing system, including radiographic, fluoroscopic, microscopic, endoscopic, loupes, naked eye, or any other suitable viewing system or instrument. After the cannulated needle and stylet are inserted into the vertebra, the inner stylet is withdrawn with the cannulated outer needle remaining engaged to the vertebra. A guidewire is positioned through the cannulated outer needle and engaged in the vertebra. The outer needle is then withdrawn so that the guidewire remains in place. The tissue around the guidewire is sequentially dilated with a number of tubular dilators of increasing diameter. When desired opening size is obtained, the guidewire and inner dilators are removed and the last inserted dilator provides a protected pathway to the pedicle or other targeted portion of the vertebra. The anchor assembly can then be positioned through the dilated pathway and engaged to the vertebra. The procedure is then repeated to position the desired number of anchor assemblies, whether it be two, three or four or more. Incisions can be made between the adjacent anchor assemblies to provide a pathway for insertion of the connecting member. Alternatively, the connecting member can be inserted axially into one of the extended receivers and then manipulated below the skin and musculature by rotating it to extend between the anchor assemblies, avoiding incisions through the skin and musculature between the anchor assemblies.

In another embodiment, the anchor assemblies are inserted percutaneously without sequential dilation. The guidewire is positioned as discussed above, and the anchor can be cannulated for positioning over the guidewire. The anchor and extended receivers are assembled and then positioned together over the guidewire, which guides the anchor assembly to the pedicle or other targeted portion of the vertebra. A cannulated driver tool is positioned over the guidewire and through the extended receiver to engage the head of the anchor and drive it into the vertebra.

In another embodiment, a pathway to the target location is prepared as discussed above. The guidewire and any dilators are removed. A cannula or other suitable retractor may remain in the incision to provide a protected pathway to the target location, although direct insertion through a micro-incision is also contemplated. An anchor driver is inserted through the extended receiver and engaged to the head of the anchor. The anchor driver can maintain the anchor in rigid alignment with the axis of the extended receiver if the anchor assembly is multi-axial. The anchor and extended receiver are inserted percutaneously to the target location of the vertebra, such as the pedicle. Insertion and alignment of the anchor assembly may be monitored fluoroscopically or with any suitable surgical navigation system. The anchor is then engaged to the vertebra at the target location with the extended receiver extending proximally therefrom through the skin level of the patient. Anchor assembly insertion and engagement is repeated for each vertebra along the instrumented levels.

In any embodiment, placement of the anchor assemblies can be conducted through a micro-incision, through a retracted opening formed in the tissue approaching the targeted location on the vertebra, or through a tubular member providing a protected passageway to one or more of the adjacent vertebrae. It is also contemplated that nerve monitoring can be performed through the extended receivers to guide placement of the anchors in the appropriate locations in the vertebrae. In one embodiment, the anchor assemblies are engaged to pedicles of the respective vertebrae. Each pedicle can be drilled and, if necessary or desired, tapped to receive a threaded screw portion of the anchor assembly. Formation and tapping of the holes in the pedicles can be monitored with an electrical stimulus applied through a guidewire, tap, probe, or anchor driver prior to and during anchor assembly insertion. Response of the patient can be monitored to determine that anchor placement does not impinge upon any nerves. The guidewire, tap, probe, driver or other instrument can be placed through a sleeve or dilator made from plastic material to provide a non-conductive insulator. In still a further form, an electrical signal is applied through the anchor assembly to guide placement of the anchor into the vertebrae without impinging on neural structures. The extended receivers can be insulated with a protective, non-conductive coating, sleeve or other layer to prevent the current from straying.

While the invention has been illustrated and described in detail in the drawings and foregoing description, the same is to be considered as illustrative and not restrictive in character, and that all changes and modifications that come within the spirit of the invention are desired to be protected.

What is claimed is:

1. An anchor assembly for securing an elongate connecting member along the spinal column, comprising:
a distal anchor for engaging bony structure and an extended receiver extending proximally from said anchor, said extended receiver including a distal implantation portion adjacent said anchor, said implantation portion being sized and shaped to receive the connecting member therein, said extended receiver further including a guide portion extending proximally from said implantation portion along a central axis, wherein said implantation portion includes opposite side members and said guide portion includes opposite arms defining a channel therebetween and said opposite arms each include a distal end formed as a single unit with a proximal end of a respective one of said side members at a break-off region, said break-off region providing a separation location for separation of said arms from said respective side member upon application of a threshold force to said arms, said separation location providing a recessed surface in an inner side of each of said arms and said respective side member that interrupts an internal thread profile extending along said inner side of each of said arms and said respective side member, wherein said recessed surface forms a groove extending into said inner side of said respective arm that extends outwardly from a major diameter of said internal thread profile thereof so that the extension of said groove in said inner side of said arm is greater than the major diameter of said internal thread of said arm and said respective side member.

2. The assembly of claim 1, wherein said channel extends through and opens at proximal ends of said arms.

3. The assembly of claim 2, wherein said channel is sized and shaped to receive said connecting member through said proximal end opening thereof in a transverse orientation to said central axis.

4. The assembly of claim 1, wherein each of said break-off regions includes a wall thickness reduced comparatively to an adjacent wall thickness of said respective arm and said respective side member, 5. The assembly of claim 1, wherein said recessed surface is further formed in an outer surface of said guide portion at said separation location and extends completely about said arm and said side member.

6. The assembly of claim 1, further comprising an engaging member positionable in said extended receiver, said engaging member including an externally threaded portion threadingly engageable with said internal thread profiles along said arms and said side members.

7. An anchor assembly for securing an elongate connecting member along the spinal column, comprising:
a distal anchor and an extended receiver extending proximally from said anchor, said extended receiver including a distal implantation portion adjacent said anchor, said extended receiver further including a guide portion extending proximally from said implantation portion along a central axis, wherein said implantation portion includes opposite side members and said guide portion includes opposite arms each defining a channel therebetween for receiving the connecting member therethrough, wherein each of said side members defines an internal thread profile in an inner side thereof along said implantation portion and each of said arms defines an internal thread profile in an inner side thereof adjacent a distal end thereof along only a portion of a length of said arm, said internal thread profile forming an extension of the thread profile of said side members, wherein said distal ends of each of said arms is joined to proximal ends of said respective side member as a single unit therewith at a reduced thickness region in said inner sides of said arm and said side member between said internal thread profiles of said arm and said side member, said reduced thickness region defining a separation location for separation of said arm from said respective side member upon application of a threshold force to said arm, wherein said reduced thickness region is formed by a groove in said inner side of said arm, said groove extending into said inner side of said arm outwardly from a major diameter of said inner thread profile thereof so that extension of said groove in said inner side of said arm is greater than the major diameter of said internal thread of said arm and said respective side member.

8. The assembly of claim 7, wherein said anchor is pivotally coupled to said extended receiver.

9. The assembly of claim 7, wherein said reduced thickness portion forms a recessed surface in said outer surface at said separation location that extends completely about said arm and said side member.

10. The assembly of claim 7, further comprising an engaging member positionable in said extended receiver, said engaging member including an externally threaded portion threadingly engageable with said internal thread profiles along said arms and said side members.

11. An anchor assembly for securing an elongate connecting member along the spinal column, comprising:
a distal anchor engageable to bony structure and an extended receiver extending proximally from and pivotally coupled to said anchor, said extended receiver including a distal implantation portion adjacent said anchor sized and shaped to receive the connecting member therein, said extended receiver further including a proximal guide portion including a pair of removable arms extending along a central axis, said arms extending proximally from and including distal ends formed as a single unit with proximal ends of a respective one of a pair of opposite side members of said implantation portion, said arms defining a channel extending therebetween from said implantation portion through proximal ends of said pair of arms, said channel including a thread profile along only a distal portion of said arms, and said channel being sized and shaped to receive the connecting member through said proximal end opening thereof in a transverse orientation to said central axis, wherein each of said side members defines an internal thread profile along said implantation portion and each of said arms defines an internal thread profile adjacent a distal end thereof that forms an extension of the thread profile of said side members and each of said arms is joined to said respective side member at a break-off region between said internal thread profile of said side member and said internal thread profile of said arm, said break-off region including a groove in an inner side of side member that extends outwardly from a major diameter of said internal thread profile into said arm so that the extension of said groove in said inner side of said arm is greater than the major diameter of said internal thread of said arm and said respective side member, and said break-off regions forms a recessed surface between said respective arm and said respective side member that extends completely about said arm and said side member.

12. The assembly of claim 11, wherein said anchor includes a head pivotally captured in said implantation portion of said extended receiver, said anchor further including a shaft extending through a distal opening through said implantation portion for engaging the bony structure.

13. The assembly of claim 12, further comprising a crown positioned about said head of said anchor in said implantation portion.

14. The assembly of claim 11, wherein each of said arms includes a length extending from said respective side member that is at least 30 millimeters.

15. The assembly of claim 11, further comprising an engaging member positionable in said extended receiver, said engaging member including an externally threaded portion threadingly engageable with said internal thread profiles along said arms and said side members.

* * * * *